United States Patent
Bae et al.

(10) Patent No.: US 7,630,079 B2
(45) Date of Patent: Dec. 8, 2009

(54) EQUIPMENT AND METHOD FOR MEASURING TRANSMITTANCE OF PHOTOMASK UNDER OFF AXIS ILLUMINATION

(75) Inventors: Suk-Jong Bae, Seoul (KR); Myoung-Soo Lee, Gyeonggi-do (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 111 days.

(21) Appl. No.: 11/936,627

(22) Filed: Nov. 7, 2007

(65) Prior Publication Data

US 2008/0130002 A1    Jun. 5, 2008

(30) Foreign Application Priority Data

Dec. 1, 2006    (KR)    ................ 10-2006-0120947

(51) Int. Cl.
G01N 21/00 (2006.01)
G01N 21/88 (2006.01)
G02F 1/33 (2006.01)
B23K 26/067 (2006.01)

(52) U.S. Cl. ............... 356/432; 356/237.4; 219/121.73; 359/305

(58) Field of Classification Search ......... 356/600–601, 356/237.1–237.5, 141.4, 5.1, 5.11, 432; 219/121.73, 219/121.74; 359/305, 308, 311–312
See application file for complete search history.

(56) References Cited

U.S. PATENT DOCUMENTS

| | | | | |
|---|---|---|---|---|
| 4,218,142 A | * | 8/1980 | Kryger et al. | 356/394 |
| 4,541,694 A | * | 9/1985 | Sullivan et al. | 359/305 |
| 4,906,099 A | * | 3/1990 | Casasent | 356/394 |
| 5,034,627 A | * | 7/1991 | Ayral et al. | 359/305 |
| 5,065,008 A | * | 11/1991 | Hakamata et al. | 250/216 |
| 5,576,880 A | * | 11/1996 | Chang | 359/305 |

(Continued)

FOREIGN PATENT DOCUMENTS

JP    2005-011461    1/2005

(Continued)

OTHER PUBLICATIONS

English language abstract of Korean Publication No. 2002-0025222.

(Continued)

*Primary Examiner*—Sang Nguyen
(74) *Attorney, Agent, or Firm*—Volentine & Whitt, PLLC

(57) ABSTRACT

Provided are equipment and a method for measuring a transmittance of a photomask. The system includes an acoustic optical deflector (AOD) substrate interposed between a light source and the photomask. The AOD is adapted to deflect a laser beam to an oblique incidence angle with respect to a surface of the photomask. A radio frequency (RF) signal source is coupled with the AOD substrate. Varying the frequency of the signal applied to the AOD substrate acts to change the refractive degree of the substrate, thereby changing an angle of deflection of the incident laser beam. A photodetector is positioned to receive the laser beam passing through the photomask and is adapted to measure an intensity of the laser beam which has penetrated the photomask. As a result, a transmittance of the photomask can be measured under off axis illumination (OAI).

21 Claims, 2 Drawing Sheets

U.S. PATENT DOCUMENTS

| | | | | |
|---|---|---|---|---|
| 5,633,747 A | * | 5/1997 | Nikoonahad | 359/312 |
| 6,271,924 B1 | * | 8/2001 | Ngoi et al. | 356/489 |
| 6,363,166 B1 | * | 3/2002 | Wihl et al. | 382/144 |
| 6,466,315 B1 | * | 10/2002 | Karpol et al. | 356/237.4 |
| 6,559,953 B1 | * | 5/2003 | Davids | 356/521 |
| 6,731,384 B2 | * | 5/2004 | Ohshima et al. | 356/237.2 |
| 6,750,960 B2 | * | 6/2004 | Bowers | 356/141.4 |
| 6,809,290 B2 | * | 10/2004 | Gross et al. | 219/121.73 |
| 6,836,560 B2 | * | 12/2004 | Emery | 382/145 |
| 6,867,888 B2 | * | 3/2005 | Sutherland et al. | 359/15 |
| 2006/0071143 A1 | | 4/2006 | Saggau et al. | |

FOREIGN PATENT DOCUMENTS

| | | |
|---|---|---|
| JP | 2005-326549 | 11/2005 |
| KR | 2002-0025222 | 4/2002 |

OTHER PUBLICATIONS

English language abstract of Japanese Publication No. 2005-011461.
English language abstract of Japanese Publication No. 2005-326549.

* cited by examiner

EQUIPMENT AND METHOD FOR MEASURING TRANSMITTANCE OF PHOTOMASK UNDER OFF AXIS ILLUMINATION

CROSS-REFERENCE TO RELATED PATENT APPLICATION

This application claims the benefit of Korean Patent Application No. 10-2006-0120947, filed on Dec. 1, 2006, in the Korean Intellectual Property Office, the disclosure of which is incorporated herein in its entirety by reference.

BACKGROUND OF THE INVENTION

1. Field of the Invention

The present invention relates to equipment and a method for fabricating a semiconductor device, and more particularly, to equipment and a method for measuring a transmittance of a photomask used in a photolithography process.

2. Description of the Related Art

Photomasks are used in microchip fabrication to form tiny circuit patterns on semiconductor substrates. Such photomasks typically include a light transmissive substrate such as quartz having deposited thereon a pattern of chrome defining a light blocking pattern.

In photolithography manufacturing, wafer circuit patterns are manufactured by projecting a pattern of light onto the photosensitive coating atop a wafer. The light pattern is formed by interposing the photomask between the light source and the wafer. Focused light from the source passes through the transmissive portions of the photomask but are blocked by the chrome pattern on the photomask.

Continuing manufacturing advances have decreased the size of these circuits and the critical dimensions (CD) of the circuit and photolithographic patterns. Several techniques have been developed to address problems with manufacturing semiconductor devices with small critical dimensions.

In a first technique, femto-second pulses from a laser are used to create correcting elements within the photomask that improve the uniformity of light transmission across the entire photomask. Improved uniformity is key to ensuring precise formation of patterns on the photomask and prevention of errors during the manufacturing process.

The correcting elements have varying characteristic depending upon the need. For example, the correcting elements may have a diameter of about 1 µm and a depth of about 30 µm. Furthermore, the correcting elements may be formed in a repeated structure and pitches of the correcting element may be adjusted to adjust the transmittance of the light transmissive substrate. Regions of the correcting elements with a small pitch have denser correcting elements, thereby lowering the transmittance compared to regions using correcting elements with a large pitch. A relationship between the pitches of the correcting elements and the transmittance of the light transmissive substrate can be observed using transmittance measuring equipment in exposure equipment for fabricating a photomask.

The second technique for reducing errors in small critical dimension photomasks is the use of off-axis illumination (OAI). Whereas conventional illumination through the photomask has been perpendicular to its surface, illumination through the photomask using off-axis light has been found to result in a higher resolution and a deeper depth-of-focus (DOF) margin.

Conventional techniques for OAI include either tilting the laser with respect to the photomask surface, or tilting the photomask itself. Each of these techniques, however, has a drawback in that the stage used to mount either the tilting laser or tilting photomask must be controlled with extremely tight tolerances. As a result, it has been extremely difficult to achieve accurate control of off-axis illumination through the photomask to measure the uniformity of its transmittance.

Accordingly, the need remains for methods and system which achieve more accurate control of OAI through a photomask.

SUMMARY OF THE INVENTION

The present invention provides equipment and a method for measuring a transmittance of a light transmissive substrate of a photomask, including ones having correcting elements for correcting the transmittance according to an incident angle of light.

According to an aspect of the present invention, there is provided a system for measuring the transmittance of a photomask. The system includes an acoustic optical deflector (AOD) substrate interposed between a light source and the photomask. The AOD is adapted to deflect a laser beam to an oblique incidence angle with respect to a surface of the photomask. A photodetector is positioned to receive the laser beam passing through the photomask and is adapted to measure an intensity of the laser beam which has penetrated the photomask. A radio frequency (RF) signal source is coupled with the AOD substrate. Varying the frequency of the signal applied to the AOD substrate acts to change the refractive degree of the substrate, thereby changing an angle of deflection of the incident laser beam.

According to another embodiment of the present invention, there is provided a method of measuring a transmittance of a photomask. The method includes deflecting a laser beam from a path normal to a surface to the photomask using an acoustic optical deflector (AOD) substrate. The deflected laser beam is then passed through the photomask. A photodetector is positioned under the photomask in a path adapted to receive and measure the intensity of the laser beam passing through the photomask.

Preferred embodiments of the invention additionally include varying a frequency of the RF signal applied to the AOD substrate to further adjust an angle of deflection of the laser beam through the AOD substrate. The photodetector is then moved in synchronicity with the change in source signal frequency by a degree mirroring the angle of deflection. The photodetector then measure the intensity of the laser beam passing through the photomask to determine its transmissivity.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art.

Figure 1:
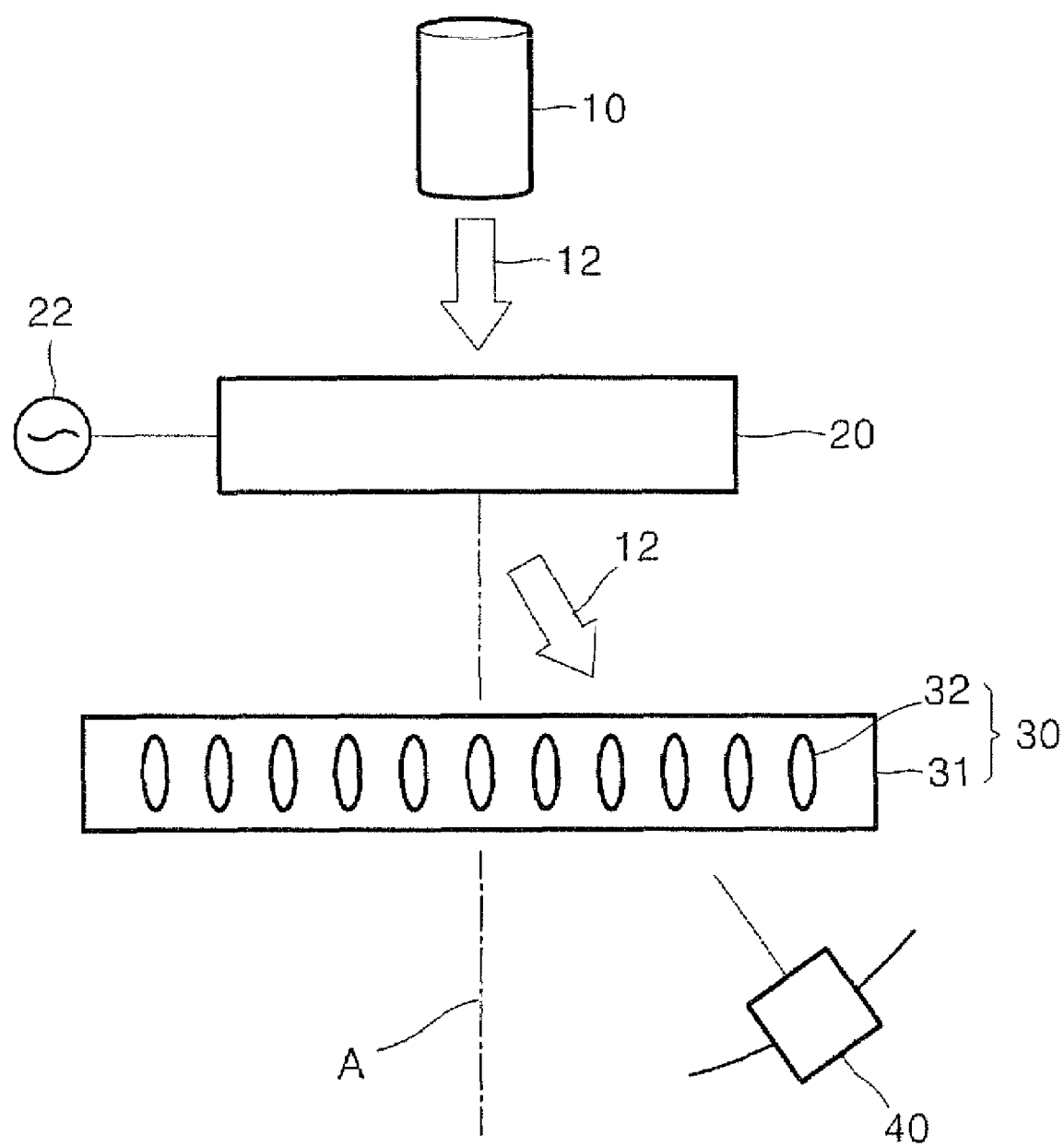
FIG. 1 is a view illustrating a schematic structure of equipment for measuring a transmittance of a photomask according to an embodiment of the present invention.

FIG. 1 is a view illustrating a schematic structure of equipment used for measuring a transmittance of a photomask according to an embodiment of the present invention. The equipment may be included with exposure equipment for fabricating the photomask. An acoustic optical deflector (AOD) substrate 20 is positioned between a light source 10 and a photomask 30. The light source 10 may include an exposure light source such as an ArF laser or a KrF laser, similar or identical to the exposure light source for exposing a wafer.

The AOD substrate 20 may be formed of a crystal such as $LiNbO_3$, $BaTiO_3$, $TeO_2$, or GaP and deflect an incident laser beam. A refractive index of the crystal of the AOD substrate 20 is varied at minute periods according to a radio frequency (RF) signal 22 applied from an external source to form an optical element. The optical element interferes with a laser beam 12 incident onto the AOD substrate 20 to refract the laser beam 12. Also, the refracted degree of the laser beam 12 may be adjusted by a frequency of the RF signal 22 applied to an AOD driver. Thus, the frequency of the RF signal 22 applied to the AOD substrate 20 may be varied in order to vary a deflection angle of the laser beam 12 penetrating the AOD substrate 20. As a result, the angle of the laser beam 12 incident onto the photomask 30 can be adjusted. Here, the AOD substrate 20 may be parallel with the photomask 30.

An OAI method is used to improve a resolution and a depth-of-focus (DOF) margin during an exposure of a wafer. Here, a laser beam having passed a modified illumination system for an OAI may be incident at an angle between 2° and 12°, and preferably 4° and 11°, with respect to a vertical axis or an optical axis A of the photomask. A transmittance of a light transmissive substrate of a photomask in which correcting elements for correcting a transmittance are formed may be varied during OAI according to an incident angle of a laser beam. An AOD substrate may be used during a measurement of a transmittance of the photomask including the correcting elements to realize such an OAI.

The laser beam 12 deflected by the AOD substrate 20 penetrates a light transmissive substrate 31 and then reaches a photodetector 40 positioned under the photomask 30.

The photomask 30 may include correcting elements 32 which are formed to predetermined pitches in the light transmissive substrate 31 to correct the transmittance of the light transmissive substrate 31. As practiced in the prior art, high energy may be applied for a short time through an irradiation of a pulse laser having a femto-second lasting time onto a light transmissive substrate to change a property of the light transmissive substrate so as to form correcting elements. The correcting elements 32 may be formed in repeated solid structures, each having a diameter of about 1 μm and a depth of about 30 μm. Also, pitches of the correcting elements 32 can be adjusted to adjust the transmittance of the light transmissive substrate 31. The photomask 30 may be a phase shift mask (PSM) or a binary mask (BM).

The photodetector 40 is a photoelectric converting device that converts light energy into electrical energy and generally includes a photodiode. The photodetector 40 measures an intensity of the laser beam 12 having penetrated the light transmissive substrate 31 and compares the intensity of the laser beam 12 with an intensity of a laser beam which has not penetrated the light transmissive substrate 31. This measured ratio is equivalent to the transmittance of the light transmissive substrate 31. Here, the photodetector 40 may use a beam splitter (not shown) positioned between the AOD substrate 20 and the photomask 30 to measure an intensity of light penetrating a transparent substrate and an intensity of light penetrating the photomask 30 so as to measure the transmittance in situ.

The photodetector 40 may move in a circular arc from a point of the AOD substrate 20 on which the laser beam 12 is incident, so as not to vary a path length of the laser beam 12. The laser beam has a deflection angle varied by the AOD substrate 20 according to the RF signal 22, penetrates the photomask 30, and reaches the photodetector 40. Here, the photodetector 40 may synchronize with the RF signal 22 to move with an adjustment of its angle from an optical axis A. In other words, the photodetector 40 may move from the optical axis A to cope with the deflection angle of the laser beam 12 caused by the AOD substrate 20. Thus, differences in a transmittance of the laser beam 12 depending on incident angle of the laser beam 12 onto the photomask 30 may be compared with one another.

Also, the photodetector 40 can be positioned under the photomask 30 to move above a plane parallel with a plane of the photomask 30. As a result, the photodetector 40 can measure the entire photomask 30. Uniformity of a transmittance of the photomask 30 can be measured through the measurement of the transmittance of the entire photomask 30.

Figure 2:
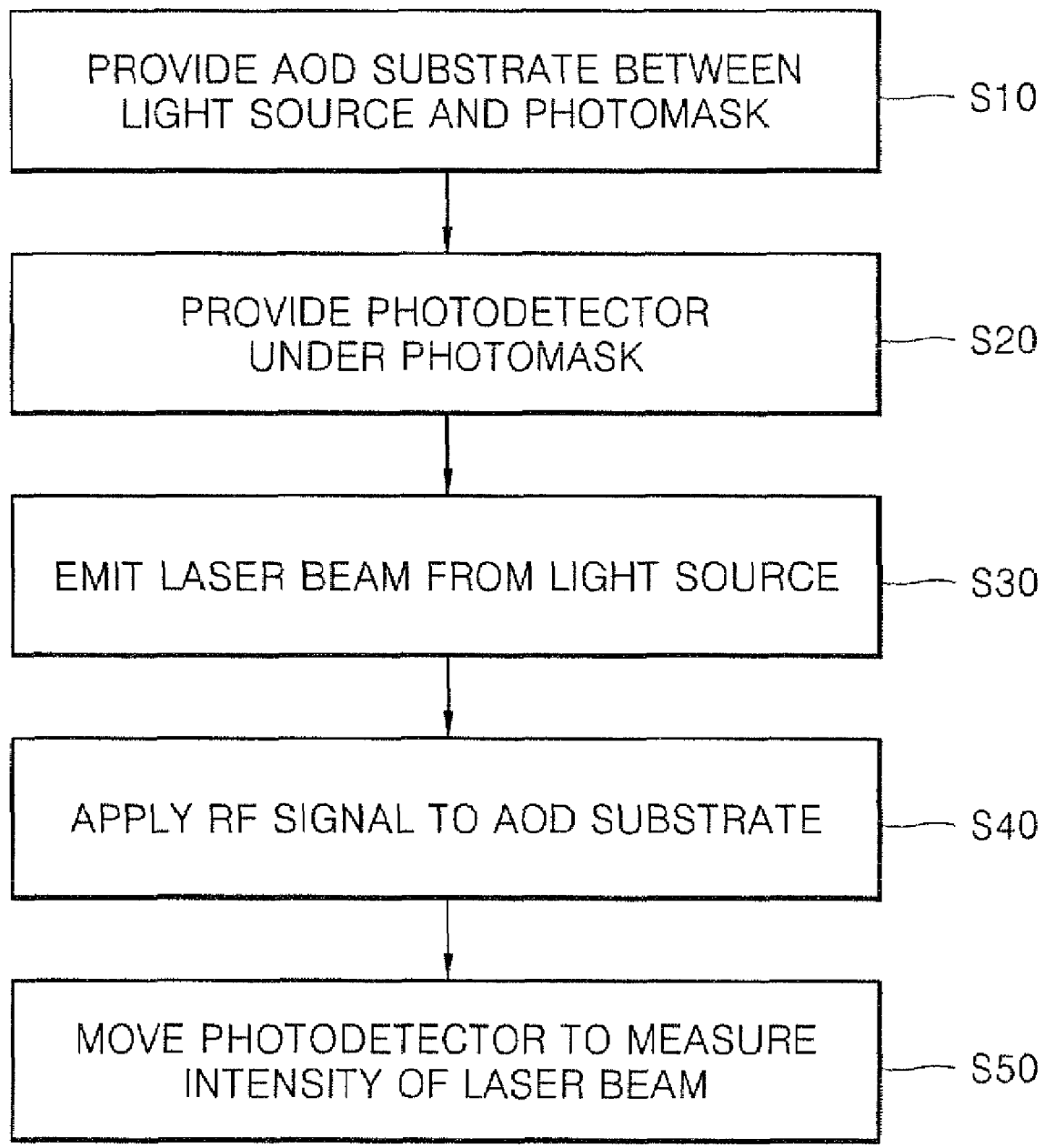
FIG. 2 is a flowchart of a method of measuring a transmittance of a photomask according to an embodiment of the present invention.

FIG. 2 is a flowchart of a method of measuring a transmittance of a photomask according to an embodiment of the present invention. Referring to FIGS. 1 and 2, in operation S10, the AOD substrate 20 is provided between the light source 10 and the photomask 30 in the equipment for measuring the transmittance of the photomask. In operation S20, the photodetector 40 is provided under the photomask 30, to measure an intensity of light penetrating the photomask 30, i.e., an intensity of a laser beam. This can occur during, before, or after the AOD substrate 20 is provided. The AOD substrate 20 and the photodetector 40 may be included within the exposure equipment for fabricating the photomask, or may be provided as different equipment from the exposure equipment.

In operation S30, the light source 10 irradiates the laser beam 12 onto the AOD substrate 20. In operation S40, the RF signal 22 is applied to the AOD substrate 20 to deflect the laser beam 12 from the AOD substrate 20 at a predetermined angle. As described above, an ArF laser or a KrF layer may be used as a light source used in wafer exposure equipment. The frequency of the RF signal 22 applied to the AOD substrate 20 can be adjusted to adjust the deflection angle of the laser beam 12. The deflection angle may be within a range between 2° and 12°, preferably, between 4° and 11°.

In operation S50, the photodetector 40 moves to cope with the deflection angle of the laser beam 12 depending on the frequency of the RF signal 22 so as to measure the intensity of the laser beam 12 penetrating the photomask 30. Here, the photodetector 40 may move in a circular arc at a predetermined distance from the point at which the laser beam 12 passes the AOD substrate 20. Moving the detector along a circular path ensures that the detected laser beam 12 has a constant path length. The photodetector 40 may move above the plane parallel with the plane of the photomask 30 to measure the intensity of the laser beam 12 so as to measure the transmittance of the entire photomask 30. Thus, the uniformity of the transmittance of the photomask 30 can be measured due to the measurement of the transmittance of the entire photomask 30.

In particular, a relationship between pitches of the correcting elements and a transmittance of the light transmissive substrate may be measured under OAI and may be used to improve critical dimension uniformity within a pattern.

The measurement of the transmittance of the photomask under the OAI can be applied to a photomask and another material of which transmittance is to be measured, e.g., a light transmissive substrate.

As described above, in equipment and a method for measuring a transmittance of a photomask under OAI according to the present invention, a laser beam can pass an AOD substrate and be deflected at a predetermined angle to realize the OAI. Also, a photodetector can be moved to cope with the deflection angle of the laser beam to measure an intensity of the laser beam penetrating the photomask. As a result, the transmittance of the photomask can be measured under the OAI.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. Equipment for measuring a transmittance of a photomask, comprising:
   an AOD (acoustic optical deflector) substrate provided between a light source and the photomask to deflect a laser beam emitted from the light source so as to allow the laser beam to be slantingly incident onto the photomask for off-axis illumination, the photomask including transmittance correcting elements, wherein the transmittance correcting elements are formed in a light transmissive substrate of the photomask and wherein the transmittance correcting elements are formed as portions having different refractive indexes from the light transmissive substrate in predetermined pitches; and
   a photodetector measuring an intensity of the laser beam which has penetrated the photomask.

2. The equipment of claim 1, wherein the AOD substrate is formed of a material comprising at least one of $LiNbO_3$, $BaTiO_3$, $TeO_2$, and GaP.

3. The equipment of claim 1, further including an RF signal source coupled with the AOD substrate and adapted to controllably vary a deflection angle of the laser beam passing through the AOD substrate responsive to a frequency of a variable RF (radio frequency) signal applied to the AOD substrate.

4. The equipment of claim 1, wherein the AOD substrate is disposed parallel with the photomask.

5. The equipment of claim 1, wherein the laser beam is slantingly incident onto the photomask at an angle between 2° and 12° from an optical axis perpendicular to the photomask.

6. The equipment of claim 5, wherein the laser beam is slantingly incident onto the photomask at an angle between 4° and 11° from an optical axis perpendicular to the photomask.

7. The equipment of claim 1, further including a beam splitter positioned between the AOD substrate and the photomask to measure the intensity of light penetrating a transparent substrate and an intensity of light penetrating the photomask so as to measure the transmittance in situ.

8. The equipment of claim 1, wherein the photodetector is adapted move above a plane at a predetermined distance from a point at which the AOD substrate meets an optical axis perpendicular to the photomask.

9. The equipment of claim 1, wherein the photodetector is adapted to move in a plane parallel with the photomask to measure the intensity of the laser beam which has penetrated the photomask.

10. The equipment of claim 1, wherein the photomask is one of a PSM (phase shift mask) and a BM (binary mask).

11. The equipment of claim 1, wherein the light source is an exposure light source of exposure equipment for fabricating a photomask.

12. A method for measuring a transmittance of a photomask, comprising:
    deflecting a laser beam from a path normal to a surface to the photomask using an acoustic optical deflector (AOD) substrate for off-axis illumination, the photomask including transmittance correcting elements;
    passing the deflected laser beam through the photomask, wherein the step of passing the deflected light through the transmittance correcting elements formed in a light transmissive substrate of the photomask and the transmittance correcting elements are formed as portions having different refractive indexes from the light transmissive substrate in predetermined pitches; and
    positioning the photodetector under the photomask in a path adapted to receive and measure the intensity of the laser beam passing through the photomask.

13. The method of claim 12, further including the step of applying an RF signal to the AOD substrate to deflect the laser beam penetrating the AOD substrate.

14. The method of claim 13, further including:
    varying a frequency of the RF signal applied to the AOD substrate to further adjust an angle of deflection of the laser beam through the AOD substrate; and
    moving the photodetector in synchronicity with the varying step in response to the angle of deflection to measure the intensity of the laser beam passing through the photomask.

15. The method of claim 14, wherein the step of moving the photodetector includes moving the photodetector above a plane at a predetermined distance from a point at which the AOD substrate meets an optical axis perpendicular to the photomask.

16. The method of claim 14, wherein the step of moving the photodetector includes moving the photodetector in a plane parallel with the photomask.

17. The method of claim 14, wherein the step of moving the photodetector includes moving the photodetector in a circular arc about a point of the AOD substrate on which the laser beam is incident so as not to vary a path length of the laser beam.

18. The method of claim 13, wherein the RF signal is applied to the AOD substrate so that the laser beam is slantingly incident onto the photomask at an angle between 2° and 12° from an optical axis perpendicular to the photomask.

19. The method of claim 18, wherein the RF signal is applied to the AOD substrate so that the laser beam is slantingly incident onto the photomask at an angle between 4° and 11° from an optical axis perpendicular to the photomask.

20. The method of claim 12, wherein the AOD substrate is formed of a material comprising at least one of $LiNbO_3$, $BaTiO_3$, $TeO_2$, and GaP.

21. The method of claim 12, wherein the photomask is one of a PSM and a BM.

* * * * *